US011657058B2

United States Patent
Sheerin et al.

(10) Patent No.: US 11,657,058 B2
(45) Date of Patent: May 23, 2023

(54) SYSTEMS AND METHODS OF ENHANCING MENTAL HEALTH AND PERFORMANCE

(71) Applicant: Citrix Systems, Inc., Ft. Lauderdale, FL (US)

(72) Inventors: Andrew Sheerin, Cambridge (GB); Ellen Rose Wootten, Bury St. Edmunds (GB); Nathan Alexander Burn, Cambridge (GB); Ronan Lewis Diver, Cambridge (GB)

(73) Assignee: Citrix Systems, Inc., Ft. Lauderdale, FL (US)

( * ) Notice: Subject to any disclaimer, the term of this patent is extended or adjusted under 35 U.S.C. 154(b) by 315 days.

(21) Appl. No.: 16/929,910

(22) Filed: Jul. 15, 2020

(65) Prior Publication Data

US 2022/0019593 A1 Jan. 20, 2022

(51) Int. Cl.
*G06F 16/2457* (2019.01)
*G06F 40/279* (2020.01)
*G06F 40/30* (2020.01)
*G06F 11/30* (2006.01)
*G06F 11/34* (2006.01)

(52) U.S. Cl.
CPC ...... *G06F 16/24575* (2019.01); *G06F 11/302* (2013.01); *G06F 11/3438* (2013.01); *G06F 40/279* (2020.01); *G06F 40/30* (2020.01)

(58) Field of Classification Search
CPC .. G06F 40/30; G06F 40/279; G06F 16/24575; G06F 11/3438; G06F 11/302; G16H 20/70; Y02A 90/10
See application file for complete search history.

(56) References Cited

U.S. PATENT DOCUMENTS 10,262,551 B2* 4/2019 DenBoer ............... G09B 19/00
2013/0159926 A1* 6/2013 Vainer ............... G06F 16/24573
715/804

(Continued)

FOREIGN PATENT DOCUMENTS

WO 2019246239 A1 12/2019

OTHER PUBLICATIONS

Docs.microsoft.com. 2020. Myanalytics FAQ—Workplace Intelligence. [online] Available at: <https://docs.microsoft.com/en-us/workplace-analytics/myanalytics/overview/mya-faq#:~:text=MyAnalytics%20uses%20data%20from%20your,email%20and%20calendar%20itself%20gets.> [Accessed Jul. 15, 2020].

(Continued)

*Primary Examiner* — Etienne P Leroux

(57) ABSTRACT

A computer system comprises a memory, a network interface, and at least one processor is provided. The memory stores a plurality of user profile records and a plurality of skill profile records. The at least one processor is configured to receive a request to recommend a skill to improve mental health of a user; retrieve, from the plurality of user profile records, a user profile record associated with the user and the skill, the user profile record including a first weight; retrieve, from the plurality of skill profile records, a skill profile record associated with the skill, the skill profile record including a second weight; determine a third weight based on the first weight and the second weight; generate a response to the request, the response including an identifier of the skill and the third weight; and transmit the response to a virtual assistant.

20 Claims, 7 Drawing Sheets

(56) References Cited

U.S. PATENT DOCUMENTS

| | | | | |
|---|---|---|---|---|
| 2014/0065585 | A1* | 3/2014 | Osborn | G09B 19/00 |
| | | | | 434/236 |
| 2017/0132371 | A1* | 5/2017 | Amarasingham | G06F 40/284 |
| 2018/0069814 | A1* | 3/2018 | Ji | H04L 51/04 |
| 2018/0248981 | A1* | 8/2018 | Salem | H04L 67/306 |
| 2020/0185096 | A1* | 6/2020 | Bantilan | H04L 67/535 |
| 2020/0229741 | A1* | 7/2020 | Hyder | G16H 20/10 |
| 2020/0273578 | A1* | 8/2020 | Kutzko | G06N 20/00 |
| 2020/0402642 | A1* | 12/2020 | Hasselberg | G16H 80/00 |
| 2021/0027897 | A1* | 1/2021 | Rasochova | A61B 5/0013 |
| 2021/0366591 | A1* | 11/2021 | Khan | G16H 40/63 |

OTHER PUBLICATIONS

International Search Report and Written Opinion for Application No. PCT/US2021/031101 dated Aug. 23, 2021, 16 pages.

\* cited by examiner

SYSTEMS AND METHODS OF ENHANCING MENTAL HEALTH AND PERFORMANCE

BACKGROUND

Knowledge workers spend large amounts of time communicating, both textually and verbally, with many different recipient and in many different venues. As such, many knowledge workers rely on information technology to boost their productivity. For instance, some knowledge workers rely virtual workspaces to help them organize and complete their work. A virtual workspace is a software framework designed to deliver and manage a user's applications, data, and desktops in a consistent and secure manner, regardless of the user's device or location. Virtual workspaces enhance the user experience by streamlining and automating those tasks that a user performs frequently, such as approving expense reports, confirming calendar appointments, submitting helpdesk tickets, and reviewing vacation requests. A virtual workspace allows users to access functionality provided by multiple enterprise applications—including "software as a service" (SaaS) applications, web applications, desktop applications, and proprietary applications—through a single interface. A virtual workspace also extends the capabilities of these applications through the use of microapps. A microapp synchronizes data from complex enterprise applications to streamline functionality, and can therefore be understood as a streamlined use case that users can access from within a virtual workspace.

SUMMARY

In at least one example, a computer system is provided. The computer system comprises a memory, a network interface, and at least one processor coupled to the memory and the network interface. The memory stores a plurality of user profile records and a plurality of skill profile records. The at least one processor is configured to receive a request to recommend a skill to improve mental health of a user; retrieve, from the plurality of user profile records, a user profile record associated with the user and the skill, the user profile record including a first weight; retrieve, from the plurality of skill profile records, a skill profile record associated with the skill, the skill profile record including a second weight; determine a third weight based on the first weight and the second weight; generate a response to the request, the response including an identifier of the skill and the third weight; and transmit the response to a virtual assistant.

At least some examples of the computer system can include one or more of the following features. The at least one processor can be further configured to determine the first weight based on data generated by interactions between the user and one or more software applications. The one or more software applications can include one or more of a calendar application and a communications application. The at least one processor can be further configured to determine the second weight based on data generated by interactions between at least one user other than the user and one or more software applications. The at least one processor can be further configured to prompt, via the virtual assistant, the user to enter input specifying feelings regarding work; receive the input; execute a natural language process on the input to identify one or more keywords and sentiments; and generate the request to recommend the skill, the request including the one or more keywords and sentiments. To retrieve the user profile record can include to retrieve a user profile record associated with the user, the skill, and the one or more keywords and sentiments. To retrieve the skill profile record can include to retrieve a skill profile record associated with the skill and the one or more keywords and sentiments. The at least one processor can be further configured to configure the skill to the user and implement the skill using a microapp within a virtual workspace client. The at least one processor can be further configured to monitor utilization of the skill by the user; prompt the user for feedback regarding the skill; and store the feedback in the memory. The at least one processor can be further configured to determine the first weight based on the feedback. The at least one processor can be further configured to monitor utilization of the skill by at least one user other than the user; prompt the at least one user for other feedback regarding the skill; and determine the second weight based on the other feedback.

In another example, a method of enhancing mental health and performance of a user of a virtual workspace client is provided. The method includes receiving a request to recommend a skill to improve mental health of a user; retrieving, from a plurality of user profile records, a user profile record associated with the user and the skill, the user profile record including a first weight; retrieving, from a plurality of skill profile records, a skill profile record associated with the skill, the skill profile record including a second weight; determining a third weight based on the first weight and the second weight; generating a response to the request, the response including an identifier of the skill and the third weight; and transmitting the response to a virtual assistant.

At least some examples of the method can include one or more of the following features. The method can further include prompting, via the virtual assistant, the user to enter input specifying feelings regarding work; receiving the input; executing a natural language process on the input to identify one or more keywords and sentiments; and generating the request to recommend the skill, the request including the one or more keywords and sentiments. Retrieving the user profile record can include retrieving a user profile record associated with the user, the skill, and the one or more keywords and sentiments. Retrieving the skill profile record can include retrieving a skill profile record associated with the skill and the one or more keywords and sentiments. The method can further include monitoring utilization of the skill by the user; prompting the user for feedback regarding the skill; and storing the feedback in memory. The method can further include determining the first weight based on the feedback. The method can further include monitoring utilization of the skill by at least one user other than the user; prompting the at least one user for other feedback regarding the skill; and determining the second weight based on the other feedback.

In another example, a non-transitory computer readable medium storing executable sequences of instructions to implement a mental health and performance enhancement process within a virtual workspace is provided. The sequences of instructions comprising instructions to receive a request to recommend a skill to improve mental health of a user; retrieve, from a plurality of user profile records, a user profile record associated with the user and the skill, the user profile record including a first weight; retrieve, from a plurality of skill profile records, a skill profile record associated with the skill, the skill profile record including a second weight; determine a third weight based on the first weight and the second weight; generate a response to the request, the response including an identifier of the skill and the third weight; and transmit the response to a virtual assistant.

At least some examples of the non-transitory computer readable medium can include one or more of the following features. The sequences of instructions can further include instructions to prompt, via the virtual assistant, the user to enter input specifying feelings regarding work; receive the input; execute a natural language process on the input to identify one or more keywords and sentiments; and generate the request to recommend the skill, the request including the one or more keywords and sentiments. The sequences of instructions can further include instructions to monitor utilization of the skill by the user; prompt the user for feedback regarding the skill; and determine the first weight based on the feedback. The sequences of instructions can further include instructions to monitor utilization of the skill by at least one user other than the user; prompt the at least one user for other feedback regarding the skill; and determine the second weight based on the other feedback.

Still other aspects, examples and advantages of these aspects and examples, are discussed in detail below. Moreover, it is to be understood that both the foregoing information and the following detailed description are merely illustrative examples of various aspects and features and are intended to provide an overview or framework for understanding the nature and character of the claimed aspects and examples. Any example or feature disclosed herein can be combined with any other example or feature. References to different examples are not necessarily mutually exclusive and are intended to indicate that a particular feature, structure, or characteristic described in connection with the example can be included in at least one example. Thus, terms like "other" and "another" when referring to the examples described herein are not intended to communicate any sort of exclusivity or grouping of features but rather are included to promote readability.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and are incorporated in and constitute a part of this specification but are not intended as a definition of the limits of any particular example. The drawings, together with the remainder of the specification, serve to explain principles and operations of the described and claimed aspects. In the figures, each identical or nearly identical component that is illustrated in various figures is represented by a like numeral. For purposes of clarity, not every component may be labeled in every figure.

DETAILED DESCRIPTION

Figure 1:
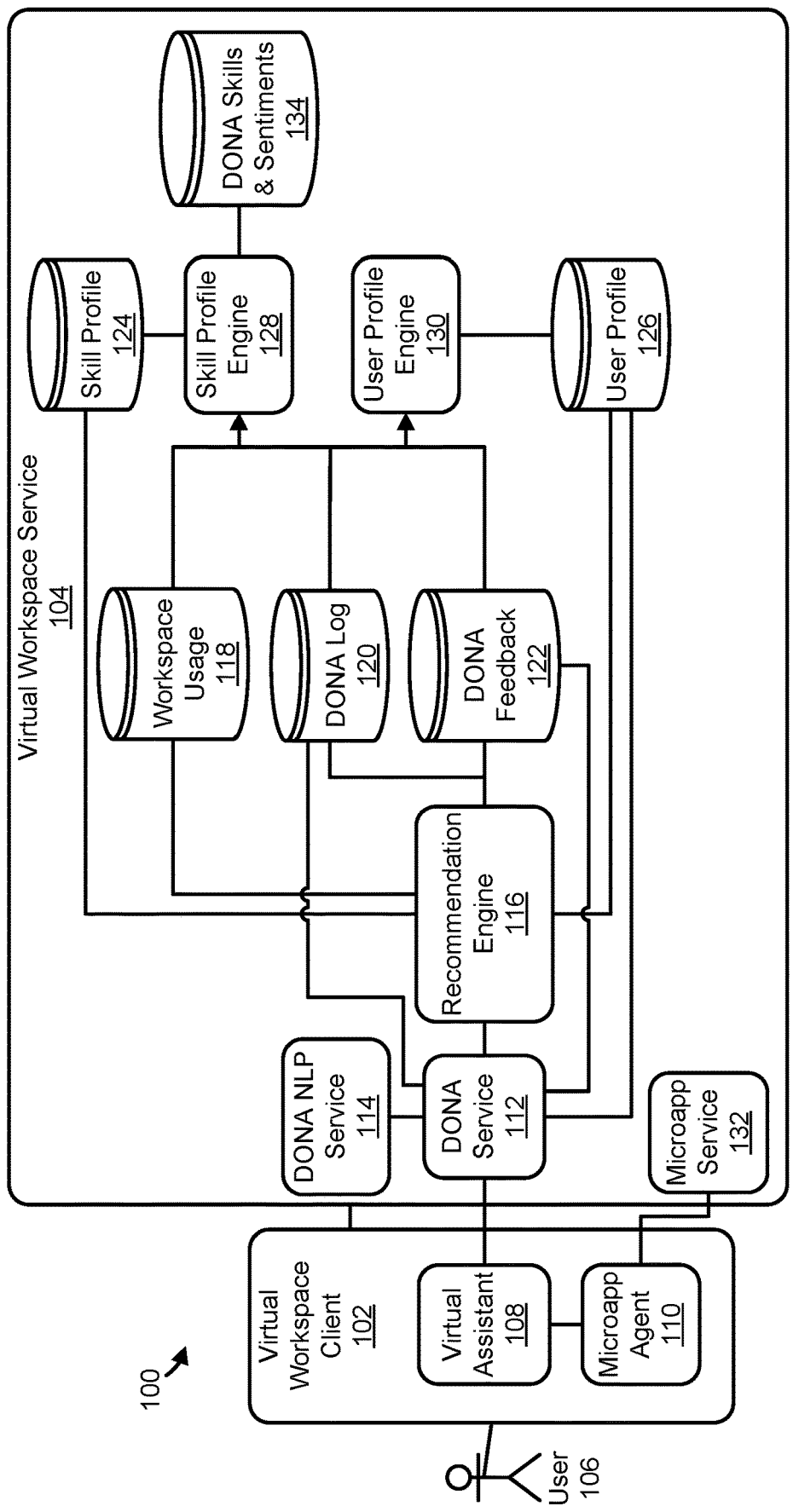
FIG. 1 is a block diagram depicting a mental health and performance system in accordance with one or more examples described herein.

As summarized above, various examples described herein are directed to systems and processes that enable a highly customizable well-being and productivity assistant that integrates seamlessly with a user's virtual workspace. Using proven psychological aids, alongside direct & indirect user feedback, the assistant will proactively safeguard the user against the stresses and challenges of the modern working landscape. The assistant will both improve the way the user works and how they feel about their work, blending productivity with well-being.

In some examples, a well-being and productivity assistant, which can referred to herein as a DONA assistant or system, interacts with a user and interoperates with other systems utilized by the user to recommend and implement skills to enhance the user's mental health and performance. The term DONA is based on a Latin phrase, "Dona nobis pacem" which means "grant use peace." DONA systems and methods, as described herein, solve initiation, tracking, and compliance problems known to plague other approaches to addressing the productivity and well-being of knowledge workers. For instance, other approaches to addressing user productivity and well-being require the worker to realize her need for assistance and seek help from others. In addition, these other approaches rely on the worker to track their efforts to comply with any assistance techniques prescribed and further rely on the worker to comply through their own effort and willpower.

However, the DONA systems and methods described herein benefit from their tight integration with a user's virtual workspace. This integration allows the DONA systems and methods to track a user's activities directly and to initiate assistance autonomously, rather than relying on the user to realize that help is needed. Moreover, the DONA systems and methods described herein can track the user's compliance with assistance techniques directly. As such, the DONA systems and method described herein are not required to rely on indirect tracking measures (e.g., journals written created separately by the user, observations written down by others, etc.). Moreover, the tight integration of the DONA systems and methods described herein enables the DONA system to exert a level of control over the user's access to applications and other users access to the user, where such control is required to enhance the user's mental health and performance. These and other examples of the technological advantages of the DONA systems and methods described herein will be understood by one of ordinary skill with the benefit of the following disclosure.

Examples of the methods and systems discussed herein are not limited in application to the details of construction and the arrangement of components set forth in the following description or illustrated in the accompanying drawings. The methods and systems are capable of implementation in other examples and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

DONA Mental Health and Performance Enhancement System

In some examples, a computer system is configured to assist users in implementing proven techniques to enhance mental health and performance. FIG. 1 illustrates a logical architecture of a DONA mental health and performance system 100 in accordance with these examples.

As shown in FIG. 1, the DONA system 100 includes a virtual workspace client 102 and a virtual workspace service 104. The virtual workspace client 102 includes a virtual assistant 108 and a microapp agent 110. The virtual workspace service 104 includes a DONA service 112, a DONA NLP service 114, a recommendation engine 116, a skill profile engine 128, a user profile engine 130, and a microapp service 132. The virtual workspace service 104 also includes a workspace usage data store 118, a DONA log data store 120, a DONA feedback data store 122, a skill profile data store 124, a user profile data store 126, and a DONA skills and sentiments data store 134. FIG. 1 also illustrates lines of communication between these computer-implemented processes and data stores. Details regarding these communications are provided below, but it should be noted that the depicted lines of communication can include inter-process communication (e.g., where two or more of the computer-implemented processes and/or data stores illustrated in FIG. 1 reside within the same execution environment) and network-based communication (e.g., where two or more of the computer-implemented processes and/or data stores reside in different execution environments coupled to one another by a computer network). In some examples, the lines of communication can include hypertext transfer protocol (HTTP) based communications. The computer-implemented process illustrated in FIG. 1 can be implemented in hardware or a combination of hardware and software.

In some examples, the workspace client 102 and the workspace service 104 are computer implemented processes that interoperate to manage and deliver applications, data, and desktops to an endpoint device of a user 106 in a consistent and secure manner, regardless of the user's device or location. The virtual workspace client 102 enhances the user experience by streamlining and automating those tasks that a user performs frequently, such as approving expense reports, confirming calendar appointments, submitting helpdesk tickets, and reviewing vacation requests. The virtual workspace client 102 allows users to access functionality provided by multiple enterprise applications—including "software as a service" (SaaS) applications, web applications, desktop applications, and proprietary applications—through a single interface.

Continuing with the DONA system 100, the virtual assistant 108, is a computer-implemented process that is configured to interact with the user 106 to execute tasks on behalf of the user. The virtual assistant 108 can receive, process, and render responses to utterances (e.g., human language communications) from the user 106. These utterances and responses can be communicated in any medium accessible to a human, with perhaps the most prominent media being sound, sight, and/or touch. As such, utterances made by the user 106 and received by the virtual assistant 108 can be communicated via vocalization, typing, gesturing, and the like. Responses can be rendered by speakers, displays, and/or haptic devices. Audio utterances can begin with an wake word, such as a name of a virtual assistant, followed by a request or statement. Audio responses can be generated by a text-to-speech program implemented by the virtual assistant 108. Using these underlying capabilities, the virtual assistant 108 can interoperate with the virtual workspace service 104 to answer questions, control devices, playback media, and execute other useful processes. In certain examples, the virtual assistant 108 is a Citrix Assistant commercially available from Citrix Systems, Inc. of Ft. Lauderdale, Fla.

Continuing with the DONA system 100, the microapp agent 110 is a computer-implemented process that is configured to interact with the user 106 to provide the user with access to targeted, specific data and functionality of one or more systems of record. These systems of record can include, for example, one or more enterprise applications that present complex, functionally-rich user interfaces that require substantial training and/or experience to navigate efficiently. To at least partially alleviate this burden, the microapp agent 110 is configured to render simple and intuitive user interfaces with a look and feel that is consistent with a container application (e.g., the workspace client 102). Generally, the user 106 can access the functionality provided by the microapp agent 110 without needing to launch a new application, toggle to a different application window, and/or navigate the elaborate user interface normally generated by a system of record. Thus, the microapp agent 110 allows the user 106 to complete simple tasks within the context of an existing application environment.

In some examples, the microapp agent 110 is configured to interoperate with the microapp service 132. In these examples, the microapp service 132 is a computer-implemented process that is configured to receive processing requests from the microapp agent 110 and to interoperate with a system of record (e.g., a more complex enterprise application) to service the processing requests received from the microapp agent 110. In at least some examples, to handle the requests received from the microapp agent 110, the microapp service 132 is configured to interoperate with a system of record via an application programming interface (API) exposed and implemented by the system of record.

Continuing with the DONA system 100, the DONA service 112 is a computer-implemented process that is configured to interoperate with the virtual assistant 108, the DONA NLP service 114, the recommendation engine 116, and the DONA feedback data store 122. The DONA service 112 is configured to orchestrate operations of the virtual assistant 108, the DONA NLP service 114, and the recommendation engine 116 to identify and implement one or more techniques to enhance the mental health and performance of the user 106. More specifically, in some examples, the DONA service 112 is configured to monitor interactions between the user 106 and the workspace client 102 for activity that indicates that the user 106 might benefit from implementation of a mental health or performance enhancement technique. In these examples, the monitoring process executed by the DONA service 112 can involve active interaction (e.g., conversations) between the DONA service 112 and the user 106 and/or passive analysis of data generated by other computer-implemented processes (e.g., scheduling software, communication software, etc.) that interact with the user 106. For instance, in certain examples, the DONA service 112 is configured to subscribe to workspace login events generated by the user 106. In these examples, the DONA service 112 can be further configured to, in response to notification of a login event, interoperate with the recommendation engine 116 to determine whether a conversation with the user 106 is warranted and to interoperate with the virtual assistant 108 to converse with the user when warranted. This conversation can being with a wellness prompt that requests the user to enter input indicating how the user is feeling about work. In some examples, the DONA service 112 can determine that a conversation is warranted where the user 106 expressly requests a conversation (e.g., via an utterance to the virtual assistant 108). In these examples, the virtual assistant 108 is configured to pass the utterance to the DONA service 112 for processing, as is described further below.

Alternatively or additionally, in some examples, the DONA service 112 can be further configured to determine that a conversation is warranted where an interval of time since a previous conversation has transpired. In these examples, the DONA service 112 can query the user profile data store 126 to retrieve records associated with the user 106. These records can include fields that store profile information for the user 106. This profile information can specify an interval (e.g., daily, bi-weekly, weekly, etc.) of time between wellness prompts that is configured for the user 106. In these examples, the DONA service 112 can also transmit a message to the recommendation engine 116 that includes a request (e.g. a last_wellness_prompt( ) API call, as described further below) for a timestamp documenting the most recent interaction between the DONA service 112 and the user 106. Upon receipt of a responsive message from the recommendation engine 116, the DONA service 112 can calculate a difference between the current time and the timestamp returned in the response, compare the difference to the interval retrieved from the user profile data store 126, and determine that a conversation is warranted where the difference exceeds the interval.

Alternatively or additionally, in some examples, the DONA service 112 can be further configured to determine that a conversation is warranted where communications and/or a schedule of the user 106 indicate fragmentation of the user's 106 time beyond a threshold value. In these examples, the DONA service 112 can transmit a message to the recommendation engine 116 that includes a request (e.g. an analyze_user( ) API call, as described further below) for the recommendation engine 116 to determine whether the user's 106 utilization of the workspace client 102 indicates that the user 106 potentially needs mental health or performance assistance. Upon receipt of a responsive message from the recommendation engine 116, the DONA service 112 determine that a conversation is warranted where the response message indicates that the user 106 potentially needs assistance.

In some examples, to converse with the user 106 the DONA service 112 is configured to receive utterances from the virtual assistant 108 and passes the utterances to the DONA NLP service 114. The DONA service 112 is also configured to receive, from the DONA NLP service 114, sentiments and keywords expressed within the utterances. These sentiments can express, for example, positive, negative, or neutral feelings in association with entities and/or intents identified by the keywords. For example, an utterance such as "stressed from constant interruptions," when passed to the DONA NLP service 114, can be returned as a negative sentiment (e.g., a sentiment value of −0.2) associated with a keyword of "interruptions."

In some examples, the DONA service 112 is configured to receive the sentiments and keywords from the DONA NLP service 114 and to pass the sentiments and keywords to the recommendation engine 116 (e.g., via a generate_recommendations( ) API call, as described further below). Further, the DONA service 112 is configured to receive, from the recommendation engine 116, one or more recommended skills to be configured and executed to enhance the mental health and performance of the user 106. These skills can implement tested and proven techniques to structure the schedule of the user 106 to increase productivity and enhance wellbeing. Continuing the example described above, to combat stress from constant interruptions, the recommendation engine 116 can return identifiers of a set of time management skills to the DONA service 112. This set of time management skills can include, for instance, a Pomodoro skill, a Smart To Do List skill, and or a Mindfulness skill.

In some examples, the DONA service 112 is configured to receive the one or more recommended skills from the recommendation engine 116, to construct a response presenting the one or more recommended skills to the user 106 for potential utilization, and to transmit the response to the virtual assistant 108. The response can include, for example, audio, text, multi-media presentations, hyperlinks, and other forms of content. It should be noted that, in some instances, utilization of a recommended skill can involve execution of the microapp agent 110 in concert with the microapp service 132. To handle events generated by utilization of at least one recommended skill, the DONA service 112 can be further configured to receive the events and to store the events in the DONA log data store 120. Examples of these events can include timestamps marking times at which the user 106 started and stopped using a skill, milestones of the skill completed or omitted by the user 106, etc. To handle optional feedback collected from the user 106 by the virtual assistant after utilization of at least one recommended skill, the DONA service 112 can be further configured to receive the feedback and to store the feedback in the DONA feedback data store 122.

Continuing with the DONA system 100, the DONA NLP service 114 is computer-implemented process configured to receive utterances and to execute natural language processing (NLP) to extract, from the utterances, sentiments and keywords. The NLP processes that the DONA NLP service 114 is configured to execute can be based on a set of heuristics, rules, and/or machine learning techniques. For instance, in certain examples, the DONA NLP service 114 is implemented by training a commercially available NLP platform (e.g., such as Google Dialogflow and Azure LUIS) to identify sentiments and keywords related to mental health and performance topics. In these examples, the NLP platform can trained using labeled training data that articulates positive, negative, and neutral sentiments about keywords (e.g., intents and/or entities) related to work activities. For instance, labeled training data can include an utterance such as "I feel overwhelmed by my current workload." This instance of training data includes the utterance, a negative sentiment for the utterance (e.g., −0.5), and an entity label for the word "workload." Many such instances of labeled training data may be required to completely train the DONA NLP service 114.

Continuing with the DONA system 100, the recommendation engine 116 is a computer-implemented process that is configured to interoperate with the DONA service 112 and to query the data stores 118-126. More specifically, the recommendation engine 116 exposes and implements an API configured to receive and handle various calls from a calling process (e.g., the DONA service 112). Theses calls can include, for example, a last_wellness_prompt( ) call, an analyze_user( ) call, and a generate_recommendations( ) call.

The last_wellness_prompt( ) call can accept parameters including an identifier of a user (e.g., the user 106). In response to reception of the last_wellness_prompt( ) call, the recommendation engine 116 can query the DONA log data store 120 to retrieve records associated with the user identifier included in the parameters. These records can include, for example, fields that store timestamps in association with log entries that characterize interactions between the user 106 and the DONA service 112. These interactions can include prompts and/or recommendations presented to the user and replies received from the user.

In some examples, during its handling of the last_wellness_prompt( ) call, the recommendation engine 116 can identify, from the retrieve records, a record storing a log entry that specifies an interaction between the user and the DONA service 112 having the most recent timestamp. Next the recommendation engine 116 can respond to the last_wellness_prompt( ) call by transmitting a response to the calling process that includes the most recent timestamp.

The analyze_user( ) call can accept parameters including an identifier of a user (e.g., the user 106) and one or more identifiers of one or more software applications utilized by the user. In response to reception of the analyze_user( ) call, the recommendation engine 116 can query the workspace usage data store 118 to retrieve records associated with the user identifier and the identifiers of the software applications included in the parameters. In some examples, the workspace usage data store 118 is maintained by a workspace analytics process, such as Citrix Analytics™ commercially available from Citrix Systems. As such, the records retrieved from the workspace usage data store 118 can include, for example, fields that store metrics that characterize the identified user's utilization of the workspace client 102 and the applications provided via the workspace client 102 that are identified in the parameters. These utilization metrics can include, for example, measures of the volume of communications (e.g., email, instant messages, voicemail, telephone conversations, etc.) processed by the user over a given time period, measures of past and future unscheduled time available to the user, measures of past and future scheduled time during which the user is unavailable, etc. For instance, in at least one example, the recommendation engine 116 retrieves utilization metrics that specify a percentage of unscheduled time on the user's 106 work calendar over the next week and a percentage of unread emails in the user's 106 inbox. Alternatively or additionally, in some examples, the recommendation engine 116 can interoperate with software applications (e.g., email, calendar, and other communications software applications) directly via one or more APIs exposed and implemented by the software applications. In these examples, the recommendation engine 116 can retrieve utilization metrics from the software applications directly and/or calculate utilization metrics based on basic data provided by the software applications.

In some examples, during its handling of the analyze_user( ) call, the recommendation engine 116 can compare the utilization metrics described above to threshold values to determine whether the user is potentially in need of assistance. For example, where utilization metrics transgress the threshold values, the user may be overly busy and in need of productivity enhancement and/or stress reduction skills. The threshold values used to make this comparison can be manually configured and/or autonomously developed and maintained by the recommendation engine 116 over time. For instance, in some examples, the recommendation engine 116 maintains threshold values including one or more of a six-month moving average value for each metric, a three-month moving average value for each metric, and a one-month moving average for each metric. Where the recommendation engine 116 determines that one or more of the utilization metrics retrieved from the workspace usage data store 118 transgresses one or more threshold values, the recommendation engine 116 can respond to the analyze_user( ) call by transmitting a response to the calling process that indicates the user is potentially in need of assistance. The response can include sentiments and keywords that indicating the source of the potential need (e.g., lack of unallocated schedule time, etc.). Where the recommendation engine 116 determines that none of the utilization metrics transgresses a threshold value, the recommendation engine 116 can respond to the analyze_user( ) call by transmitting a response to the calling process that indicates the user in not in need of assistance.

The generate_recommendations( ) call can accept parameters including an identifier of a user (e.g., the user 106), one or more keywords, and one or more sentiments associated with the one or more keywords. In response to reception of the generate_recommendations( ) call, the recommendation engine 116 can query the user profile data store 126 to retrieve records associated with the user identifier, keywords, and sentiments included in the parameters. These records can include, for example, fields that store identifiers of skills previously recommended to and/or utilized by the user in response to past utterances including the keywords and sentiments. The records can further include fields that store weights that reflect the user's past experience with the identified skill. These weights can be, for example, positive values where the user's interaction with the identified skill indicates satisfaction or the user has submitted feedback expressly endorsing of the identified skill. Conversely, the weights can be, for example, negative values where the user's interaction with the identified skill indicates dissatisfaction or the user has submitted feedback expressly disapproving of the identified skill. Further, the recommendation engine 116 can query the skill profile data store 124 to retrieve records associated with the keywords and sentiments included in the parameters. These records can include, for example, fields that store identifiers of skills designed to address the situational source of the keywords and sentiments. It should be noted that such identified skills can be identified skills that were previously recommended to and/or utilized by other users. These records can further include fields that store weights that reflect the other users' past experiences with the identified skill. These weights can be, for example, positive values where the users' interaction with the identified skill indicates satisfaction or the other users have submitted feedback expressly endorsing of the identified skill. Conversely, the weights can be, for example, negative values where the users' interaction with the identified skill indicates dissatisfaction or the other users have submitted feedback expressly disapproving of the identified skill.

In some examples, during its handling of the generate_recommendations( ) call, the recommendation engine 116 calculates an aggregate weight for each skill identified and retrieved from the skill profile data store 124 and the user profile data store 126. This aggregate weight can be a simple sum of the weights associated with the identifier of the skill in the records retrieved from the data stores 124 and 126. Alternatively, the aggregate weight can be a weighted sum that favors weights from the user profile data store 126 over weights from the skill profile data store 124 or vice versa. In these examples, the recommendation engine 116 can respond to the generate_recommendations( ) call by transmitting a response message to the calling process that includes the identifiers of the skills and the aggregate weights associate with the skill identifiers.

Figure 2:
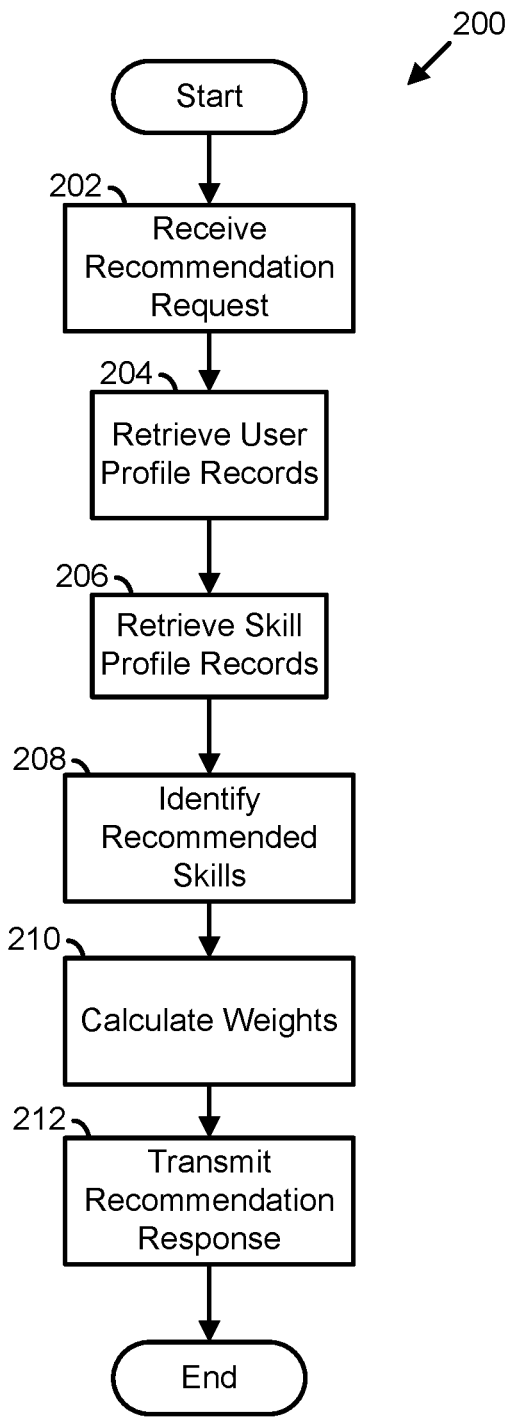
FIG. 2. is a flow diagram showing a recommendation process in accordance with one or more examples described herein.

In some examples, to process a generate_recommendations( ) call, the recommendation engine 116 is configured to execute a recommendation process, such as the process 200 illustrated in FIG. 2.

As shown in FIG. 2, the process 200 starts with a recommendation engine (e.g., the recommendation engine 116 of FIG. 1) receiving 202 a recommendation request (e.g., a generate_recommendations( ) API call) from a requesting process (e.g., the DONA service 112 of FIG. 1). The recommendation engine parses the recommendation request to identify parameters includes a user identifier, keywords, and sentiments. The recommendation engine queries a user profile data store (e.g., the user profile data store 126 of FIG. 1) to retrieve 204 records associated with the user identifier, keywords, and sentiments included in the parameters. These records can include, for example, fields that store identifiers of skills previously recommended to and/or utilized by the user in response to past utterances including the keywords and sentiments. The records can further include fields that store weights that reflect the user's past experience with the identified skill.

Continuing the process 200, the recommendation engine queries a skill profile data store (e.g., the skill profile data store 124 of FIG. 1) to retrieve 206 records associated with the keywords and sentiments included in the parameters. These records can span multiple users and can include, for example, fields that store identifiers of skills designed to address the situational source of the keywords and sentiments. It should be noted that such identified skills can be identified skills that were previously recommended to and/or utilized by other users. These records can further include fields that store weights that reflect the other users' past experiences with the identified skill.

Continuing the process 200, the recommendation engine identifies 208 recommended skills as being the skills stored in the retrieved records and calculates 210 an aggregate weight for each recommended skill based on the weights stored in the retrieved records. For instance, the recommendation engine can calculate a simple or weighted average of weights from the retrieved records.

Continuing the process 200, the recommendation engine generates and transmits 212 a recommendation response (e.g., a response to the generate_recommendations( ) call) that specifies the recommended skills and aggregates weights, and the process 200 ends.

It should be noted that the API exposed by the recommendation engine 116 is not limited to the call specified above. As such, some examples of the recommendation engine 116 include additional API calls without departing from the scope of the examples described herein.

Returning with the DONA system 100, the skill profile engine 128 is a computer-implemented process that is configured to periodically maintain the skill profile data store 124. In some examples, the skill profile data store 124 can include records that associate keywords and sentiments with skills designed to address the situational source of the keywords and sentiments. As such, the records of the skill profile data store 124 can include fields configured to store keywords, sentiments, identifiers of skills, and weights that reflect past experiences of the users of the skills. To generate and/or adjust the weights to maintain their currency in view of changing circumstances, the skill profile engine 128 can execute any of a variety of rule-based and/or machine learning processes. These processes can accept input data that identifies and characterizes users of skills, user engagement with skills, completion rates for skills, repeated skill usage, utilization metrics, and user feedback (e.g., positive, negative, and neutral) regarding skills.

Figure 3:
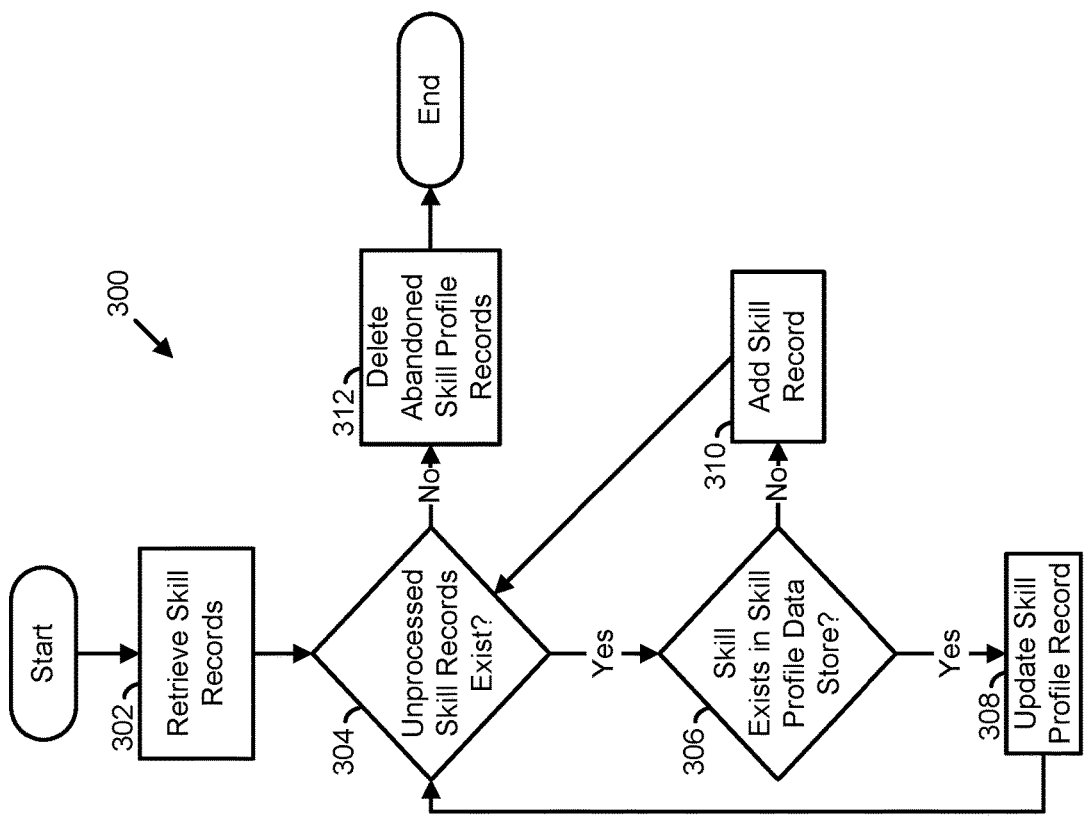
FIG. 3. is a flow diagram showing a skill profile maintenance process in accordance with one or more examples described herein.

For instance, in some examples, to maintain the skill profile data store 124, the skill profile engine 128 is configured to execute a skill profile maintenance process, such as the process 300 illustrated in FIG. 3.

As shown in FIG. 3, the process 300 starts with a skill profile engine (e.g., the skill profile engine 128 of FIG. 1) querying a skill data store (e.g., the DONA skill and sentiment data store 134 of FIG. 1) to retrieve 302 records that identify mental health and performance enhancement skills available to users. These records can include, for example, fields that store identifiers of skills, one or more keywords, and one or more sentiments.

Continuing the process 300, the skill profile engine determines 304 whether unprocessed skill records retrieved from the skill data store exist. Where the skill profile engine determines 304 that unprocessed records exist, the skill profile engine advances to the next unprocessed skill record and determines 306 whether a skill profile record corresponding to the skill record exists within a skill profile data store (e.g., the skill profile data store 124 of FIG. 1). Within the operation 306, correspondence can be determined where an identifier of the skill within the skill record matches (e.g., is the same as) an identifier of the skill within a skill profile record. In some examples, correspondence can further require matching keywords, sentiments, and/or utilization metrics within the skill record and a skill profile record. In some examples, a utilization metric within the skill recorded is identified as matching a utilization metric in a skill profile record where the utilization metrics are within an identified range (5%, 10%, 25%, 50%, etc.) of one another.

Where the skill profile engine determines 306 that no skill profile record corresponding to the skill record exists within the skill profile data store, the skill profile engine adds 310, to the skill profile data store, a new skill profile record that corresponds to the skill record. In adding 310 the new skill profile record, the skill profile engine allocates a new record within the skill profile data store and populates fields of the record with an identifier of the skill, one or more keywords associated with the skill, one or more sentiments associated with the skill, and a weight associated with the combination of skill, keywords, and sentiments. In some examples, the skill profile engine retrieves default values used to populate the fields of the skill profile record from its corresponding skill record.

Continuing the process 300, where the skill profile engine determines 306 that a skill profile record corresponding to the skill record exists within the skill profile data store, the skill profile engine updates 308 the skill profile record that corresponds to the skill record. In updating 308 the skill profile record, the skill profile engine can execute any of a variety processes to calculate new values for the weights stored in the skill profile record. These weighting processes can incorporate rules-based processes, machine learning processes, or a combination of rules-based and machine learning processes.

For instance, in some examples of the update operation 308, the skill profile engine queries a DONA log data store (e.g., the DONA log data store 120 of FIG. 1) to retrieve records associated with the combination of skill, keywords, and sentiments identified in the skill profile record. The records retrieved from the DONA log data store can span multiple users and can include fields that store completion rates for the combination of skill, keywords, and sentiments.

In these examples, the skill profile engine can adjust the weight in the skill profile record based on a statistical summarization of the completion rates stored in the retrieved records. For instance, the skill profile engine can adjust the weight downward where an average completion rate falls below a configurable threshold value and/or can adjust the weight upward where the average completion rate exceeds the configurable threshold value. Additionally or alternatively, the skill profile engine can adjust the weight based on function that is inversely proportional to the average completion rate.

Alternatively or additionally, in some examples of the update operation 308, the skill profile engine queries a DONA feedback data store (e.g., the DONA feedback data store 122 of FIG. 1) to retrieve records associated with the combination of skill, keywords, and sentiments identified in the skill profile record. The records retrieved from the DONA feedback data store can span multiple users and can include fields that store values (e.g., between −1 and +1) that indicate negative, neutral, and positive feedback entered by users of the skill for the combination of skill, keywords, and sentiments. In these examples, the skill profile engine can adjust the weight in the skill profile record based on a statistical summarization of the feedback values stored in the retrieved records. For instance, the skill profile engine can adjust the weight downward where an average feedback value falls below a configurable threshold value and/or can adjust the weight upward where the average feedback value exceeds the configurable threshold value. Additionally or alternatively, the skill profile engine can adjust the weight based on function that is directly proportional to the average feedback value.

Alternatively or additionally, in some examples of the update operation 308, the skill profile engine queries the DONA log data store and the DONA feedback data store to retrieve records associated with the combination of skill, keywords, and sentiments identified in the skill profile record. The records retrieved from the DONA log data store and the DONA feedback data store can span multiple users. Next, the skill profile engine queries a workspace usage data store (e.g., the workspace usage data store 118 of FIG. 1) to retrieve records associated with the users identified in the records retrieved from the DONA log data store and the DONA feedback data store. The records retrieved from the workspace usage data store can include fields that store utilization metrics for the users identified in the records retrieved from the DONA log data store and the DONA feedback data store. In these examples, the skill profile engine can adjust the weight in the skill profile record based on a statistical summarization of the utilization metrics stored in the retrieved records. For instance, the skill profile engine can increase the weight of a Pomodoro skill profile record to 0.8 where the total emails sent per day per user is calculated to have been be greater than 100 and calendar bookings per user is calculated to have been greater than 50%.

Alternatively or additionally, in some examples of the update operation 308, the skill profile engine queries the DONA log data store, the DONA feedback data store, and the workspace usage data store to retrieve records associated with the combination of skill, keywords, and sentiments in the skill profile record. The records retrieved from the DONA log data store, the DONA feedback data store, and the workspace usage data store can span multiple users and can include data that identifies and characterizes users of skills, user engagement with skills, completion rates for skills, repeated skill usage, utilization metrics, and user feedback (e.g., positive, negative, and neutral) regarding skills. The skill profile engine can input this data into one or more machine learning processes to output a weight that reflects the usefulness of the skill in addressing its associated keywords and sentiments. In these examples, the skill profile engine can replace the weight in the skill profile record with the output of the one or more machine learning processes.

Returning to the operation 304, where the skill profile engine determines 304 that no unprocessed skill records exist, the skill profile engine deletes 312, from the skill profile data store, records of abandoned skills (e.g., skill profile records that were not accessed during this instance of the process 300), and the process 300 ends.

Returning to the DONA system 100, the user profile engine 130 is a computer-implemented process that is configured to periodically maintain the user profile data store 126. In some examples, the user profile data store 126 can include records that associate users with skills previously recommended to and/or utilized by the user in response to the past utterances. As such, the records of the user profile data store 126 can include fields configured to store keywords, sentiments, identifiers of users, identifiers of skills, and weights that reflect the effectiveness of the skill in addressing, for the user, the situation underlying the keywords and sentiments. To generate and/or adjust the weights to maintain their currency in view of changing circumstances, the user profile engine 128 can execute any of a variety of rule-based and/or machine learning processes. These processes can accept input data that identifies and characterizes users of skills, user engagement with skills, completion rates for skills, repeated skill usage, utilization metrics, and user feedback (e.g., positive, negative, and neutral) regarding skills.

Figure 4:
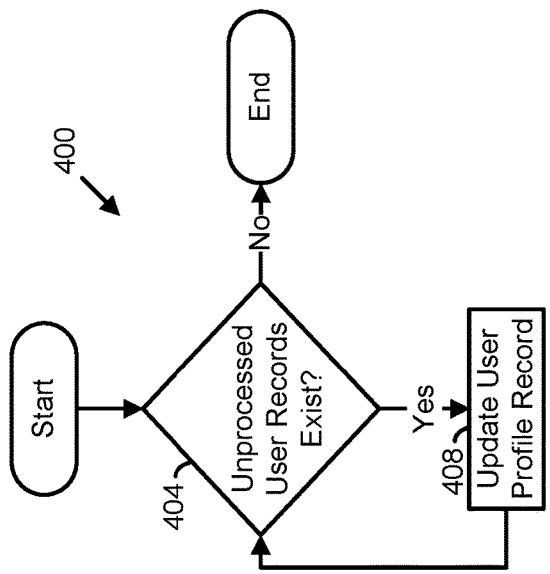
FIG. 4. is a flow diagram showing a user profile maintenance process in accordance with one or more examples described herein.

For instance, in some examples, to maintain the user profile data store 126, the user profile engine 128 is configured to execute a user profile maintenance process, such as the process 400 illustrated in FIG. 4.

As shown in FIG. 4, the process 400 starts with a user profile engine (e.g., the user profile engine 128 of FIG. 1) determining 404 whether any user records stored in a user profile data store (e.g., the user profile data store 126 of FIG. 1) have not been processed by the current instance of the process 400. Where the user profile engine determines 404 that unprocessed records exist, the user profile engine advances to the next unprocessed user profile record and updates 408 the user profile record. In updating 408 the user profile record, the user profile engine can execute any of a variety processes to calculate new values for the weights stored in the user profile record. These weighting processes can incorporate rules-based processes, machine learning processes, or a combination of rules-based and machine learning processes.

For instance, in some examples of the update operation 408, the user profile engine queries a DONA log data store (e.g., the DONA log data store 120 of FIG. 1) to retrieve records associated with the combination of the user, skill, keywords, and sentiments identified in the user profile record. The records retrieved from the DONA log data store are specific to the user and can include fields that store completion rates for the combination of skill, keywords, and sentiments. In these examples, the user profile engine can adjust the weight in the user profile record based on a statistical summarization of the completion rates stored in the retrieved records. For instance, the user profile engine can adjust the weight downward where an average completion rate falls below a configurable threshold value and/or can adjust the weight upward where the average completion rate exceeds the configurable threshold value. Additionally or alternatively, the user profile engine can adjust the weight based on function that is inversely proportional to the average completion rate.

Alternatively or additionally, in some examples of the update operation 408, the user profile engine queries a DONA feedback data store (e.g., the DONA feedback data store 122 of FIG. 1) to retrieve records associated with the combination of user, skill, keywords, and sentiments identified in the user profile record. The records retrieved from the DONA feedback data store are specific to the user and can include fields that store values (e.g., between −1 and +1) that indicate negative, neutral, and positive feedback entered by the user for the combination of skill, keywords, and sentiments. In these examples, the user profile engine can adjust the weight in the user profile record based on a statistical summarization of the feedback values stored in the retrieved records. For instance, the user profile engine can adjust the weight downward where an average feedback value falls below a configurable threshold value and/or can adjust the weight upward where the average feedback value exceeds the configurable threshold value. Additionally or alternatively, the user profile engine can adjust the weight based on function that is directly proportional to the average feedback value.

Alternatively or additionally, in some examples of the update operation 408, the user profile engine queries a workspace usage data store (e.g., the workspace usage data store 118 of FIG. 1) to retrieve records associated with the user identified in the user profile record. The records retrieved from the workspace usage data store can include fields that store utilization metrics for the user. In these examples, the user profile engine can adjust the weight in the user profile record based on a statistical summarization of the utilization metrics stored in the retrieved records. For instance, the user profile engine can increase the weight of a Pomodoro user profile record to 0.8 where the total emails sent per day by the user is calculated to have been be greater than 100 and calendar bookings of the user is calculated to have been greater than 50%.

Alternatively or additionally, in some examples of the update operation 408, the user profile engine queries the DONA log data store, the DONA feedback data store, and the workspace usage data store to retrieve records associated with the combination of user, skill, keywords, and sentiments in the user profile record. The records retrieved from the DONA log data store, the DONA feedback data store, and the workspace usage data store are specific to the user and can include data that identifies and characterizes the user, user engagement with skills, completion rates for skills, repeated skill usage, utilization metrics, and user feedback (e.g., positive, negative, and neutral) regarding skills. The user profile engine can input this data into one or more machine learning processes to output a weight that reflects the usefulness of the skill in addressing its associated keywords and sentiments. In these examples, the user profile engine can replace the weight in the user profile record with the output of the one or more machine learning processes.

Returning to the operation 404, where the user profile engine determines 404 that no unprocessed user profile records exist, the process 400 ends.

Returning to FIG. 1, it should be noted that, in some examples, the user profile engine 130 is configured to adjust the interval of time between prompting the user for their mental wellness. In these examples, the user profile engine 130 can make such adjustments based on the user's schedule and/or other activity as stored in the DONA log data store 120 and can continue to adjust until the user responds consistently to the wellness prompt.

DONA Mental Health and Performance Enhancement Processes

Figure 5A:
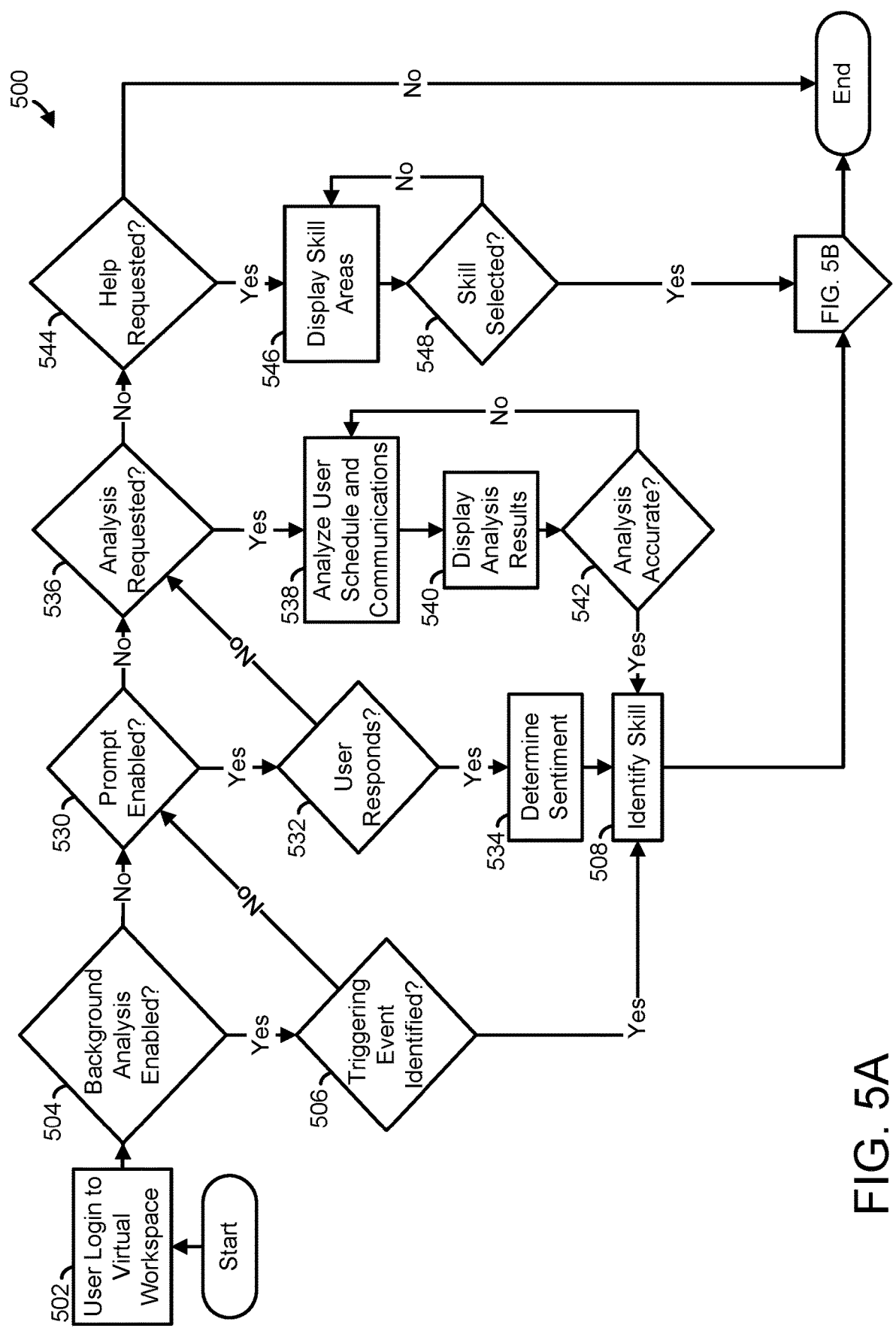
FIGS. 5A and 5B are flow diagram illustrating an orchestration process in accordance with one or more examples described herein.
Figure 5B:
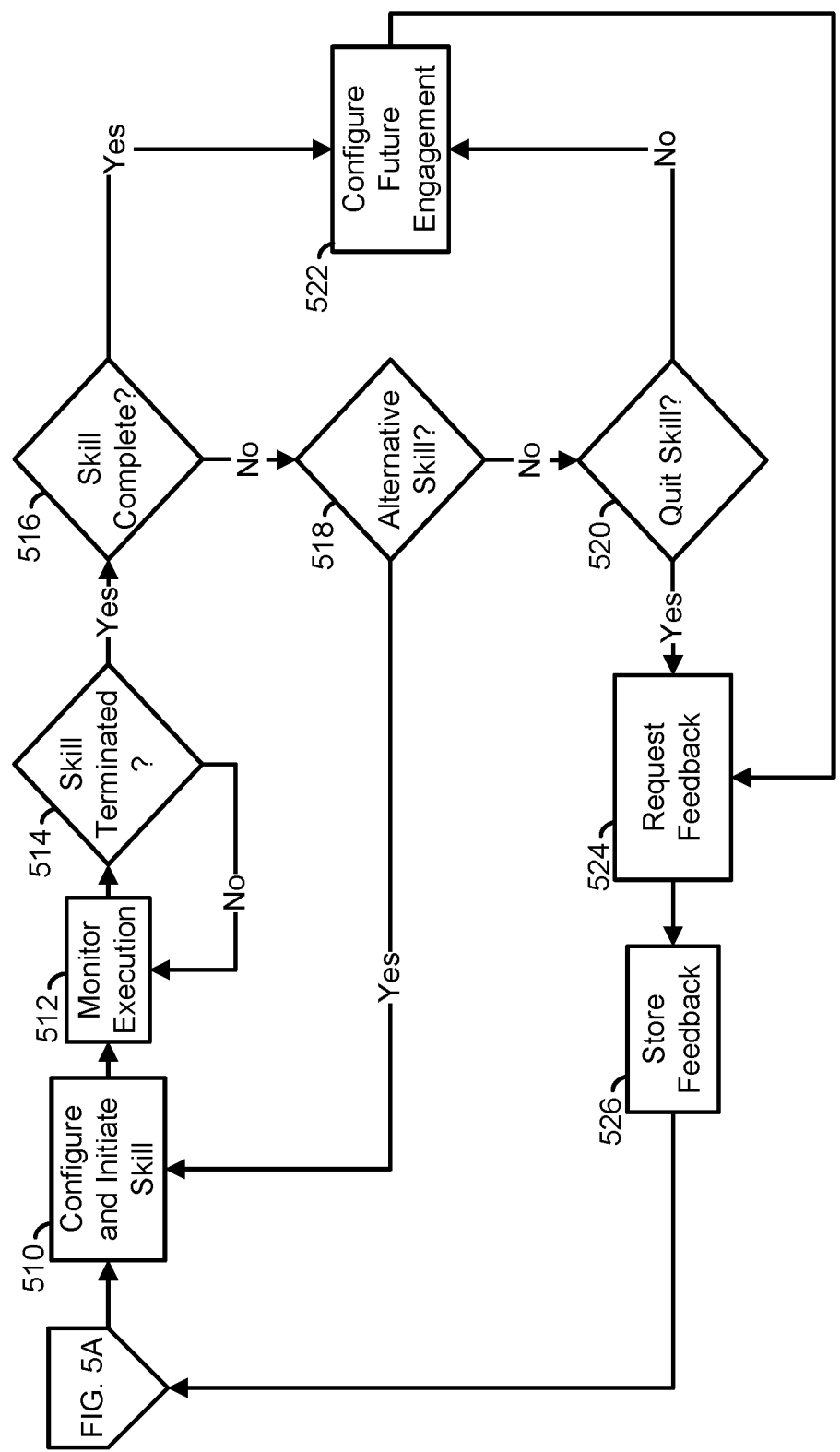

At least some examples of the DONA system 100 are configured to execute DONA mental health and performance enhancement processes. FIGS. 5A and 5B illustrate one example of a DONA process 500 that the DONA system 100 is configured to execute in some examples. As shown in FIG. 5A, the process 500 starts with a user (e.g., the user 106 of FIG. 1) logging into 502 a workspace client (e.g. the workspace client 102 of FIG. 1). During the login process, the workspace client transmits a message to a workspace service (e.g., the workspace service 104 of FIG. 1) that notifies the workspace service of the user login. The workspace service, in turn, notifies processes subscribed to receive notifications of user logins. One such process is a DONA service (e.g., the DONA service 112 of FIG. 1).

Continuing the process 500, the DONA service receives a notification of the user login from the workspace service and determines 504 whether background analysis of the user is enabled. For example, the DONA service can query a user profile data store (e.g., the user profile data store 126 of FIG. 1) to retrieve records associated with an identifier of the user. These records can store configuration information indicating whether the user wishes to have her interactions with the workspace client monitored by the DONA service. Where the DONA service determines 504 that background analysis is not enabled for the user, the DONA service proceeds to operation 530. Where the DONA service determines 504 that background analysis is enabled for the user, the DONA service proceeds to operation 506.

In the operation 506, the DONA service determines 506 whether a triggering event has been identified. For example, to determine whether a triggering event has occurred, the DONA service can transmit an analysis request (e.g., an analyze_user( ) call) to a recommendation engine (e.g., the recommendation engine 116 of FIG. 1). This analysis request can include parameters identifying the user and all of the applications utilized by the user. In this example, the DONA service determines 506 that a triggering event has been identified where an analysis response (e.g., a response to the analyze_user( ) call) received from the recommendation engine indicates that the user is potentially in need of assistance. Conversely, in this example, the DONA service determines 506 that a triggering event has not been identified where an analysis response received from the recommendation engine does not indicate that the user is potentially in need of assistance. Where the DONA service determines 506 that a triggering event has not been identified, the DONA service proceeds to operation 530. Where the DONA service determines 506 that a triggering event has been identified, the DONA service proceeds to operation 508.

In the operation 508, the DONA service identifies 508 a skill to enhance the user's mental health and performance. For example, to identify a skill, the DONA service can transmit a recommendation request (e.g., a generate_recommendations( ) call) to the recommendation engine. The recommendation request can be include keywords and sentiments received and/or identified within operations 506, 534, and/or 542 as parameters of the recommendation request. In this example, the DONA service identifies the skill as being the recommended skill in a recommendation response (e.g., a response to the generate_recommendations( ) call) received from the recommendation engine that has the highest weight.

Moving to FIG. 5B, the DONA service interoperates with a virtual assistant (e.g., the virtual assistant 108 of FIG. 1) to configure and initiate 510 the skill identified in the operation 508. Execution of the skill can involve execution of one or more microapp agents (e.g., the microapp agent 110). In some examples, the DONA service monitors 512 execution of the skill by subscribing, via the workspace service, to events generated by the skill, the virtual assistant, and the microapp agent (or its corresponding microapp service (e.g., the microapp service 132 of FIG. 1)). Alternatively or additionally, in some examples, the DONA service monitors 512 execution of the skill by periodically retrieving records associated with the user and the skill from a DONA log data store (e.g., the DONA log data store 120 of FIG. 1).

Continuing the process 500, the DONA service determines 514 whether the skill is terminated. For example, the DONA service can be notified of termination of the skill via an event received from the workspace service and/or one or more records associated with the skill and the user retrieved from the DONA log data store. These records can specify events marking milestones in execution of the skill. Where the DONA service determines 514 that the skill is not terminated, the DONA service continues to monitor 512 execution of the skill. Where the DONA service determines 514 that the skill is terminated, the DONA service proceeds to operation 516.

In the operation 516, the DONA service determines 516 whether the skill executed until completion. For example, the DONA service can query the DONA log data store to retrieve one or more records associated with the skill and the user that indicate the user completed her interaction with the skill. Where the DONA service determines 516 that the skill did not execute to completion, the DONA service proceeds to operation 518. Where the DONA service determines 516 that the skill executed to completion, the DONA service proceeds to operation 522.

In the operation 518, the DONA determines 518 whether the user would like to utilize a different skill. For instance, in some examples, the DONA service prompts the user to enter input specifying whether the user would like to utilize a different skill via the virtual assistant. The prompt can include elements selectable by the user to identify the different skill preferred by the user. In these examples, the DONA service determines 518 that the user would like to utilize a different skill in response to reception of input selecting a different skill. Where the DONA service determines 518 that the user would like to utilize a different skill, the DONA service proceeds to the operation 510 to configure and initiate the different skill. Where the DONA service determines 518 that the user does not want to utilize a different skill, the DONA service proceeds to operation 520.

In the operation 520, the DONA service determines 520 whether the user would like to quit utilizing the skill. For example, the DONA service can prompt, via the virtual assistant, the user to enter input specifying whether the user would like to quit utilizing the skill. In these examples, the DONA service determines 520 that the user would like to quit utilizing the skill in response to reception of input indicating the same. Where the DONA service determines 520 that the user would like to quit utilizing the skill, the DONA service proceeds to operation 524. Where the DONA service determines 520 that the user does not want to quit utilizing the skill, the DONA service proceeds to operation 522.

In the operation 522, the DONA service configures 522 itself for future engagement with the user. For example, the DONA service can prompt, via the virtual assistant, the user to enter input specifying whether the user would like to add the skill to her favorites, to enter input tagging the skill, and/or to enter input scheduling repeated utilization of the skill. Additionally, the DONA service can invite, via the virtual assistant, the user to read more about the skill.

In the operation 524, the DONA service requests 524 feedback regarding the skill from the user. For example, the DONA service can prompt, via the virtual assistant, the user to enter input specifying feedback regarding the skill. Continuing the process 500, the DONA skill stores 526 the feedback, for example, in a DONA feedback data store (e.g., the DONA feedback data store 122 of FIG. 1), and, returning to FIG. 5A, the process 500 ends.

Returning to the operation 530, the DONA service determines 530 whether prompting of the user by the DONA service is enabled. For example, the DONA service can query the user profile data store to retrieve records associated with an identifier of the user. These records can store configuration information indicating whether the user wishes to receive prompts from the DONA service. Where the DONA service determines 504 that prompts are not enabled for the user, the DONA service proceeds to operation 536. Where the DONA service determines 530 that prompts are enabled for the user, the DONA service proceeds to operation 532.

In the operation 532, the DONA service prompts, via the virtual assistant, the user to enter input specifying the user's state of mind. For example, the prompt can recite "how are you feeling today." The DONA service then determines 532 whether the user responded to the prompt. Where the DONA service determines 532 that the user responded to the prompt, the DONA service proceeds to operation 534. Where the DONA service determines 530 that the user did not respond to the prompt, the DONA service proceeds to operation 536.

In the operation 534, the DONA service determines, via a DONA NLP service (e.g., the DONA NLP service 114 of FIG. 1), sentiments and keywords articulated within the user's response to the prompt in the operation 532.

Returning to the operation 536, the DONA service determines 536 whether analysis of the user has been requested by the user, a timer, or some other process. For instance, in one example, the DONA service receives a notification from the virtual assistant that indicates the user entered input expressly requesting DONA analysis. In some examples, the user input can be in response to a prompt. In these examples, the DONA service determines 536 that analysis of the user has been requested in response to receive of the notification. Where the DONA service determines 536 that analysis of the user has been requested, the DONA service proceeds to operation 538. Where the DONA service determines 536 that analysis of the user has not been requested, the DONA service proceeds to operation 544.

In the operation 538, the DONA service prompts, via the virtual assistant, the user to enter input specifying configuration information for an analysis of the user. The prompt to the user can include elements selectable by the user to specify analysis of the user's interactions with various software application provided via the workspace client. These software applications can include, for example, calendar, email, instant messaging, and other communication applications (e.g., Slack). Next the DONA service analyzes 538 the user's activity by transmitting an analysis request (e.g., an analyze_user( ) call) to the recommendation engine. This analysis request can include parameters identifying the user and the software applications selected by the user. The DONA service next receives an analysis response.

Continuing the process 500, the DONA service parses the analysis response and displays 540, via the virtual assistant, results of the analysis response. These results can include sentiments and keywords descriptive of areas of potential need for the user. Next, the DONA service determines 542 whether the analysis is accurate. For instance, in one example, the DONA service prompts, via the virtual assistant, the user to enter input specifying whether the user would like to refine the analysis or utilize a recommend skill. Where the DONA service receives input indicating that the user would like to utilize the recommended skill, the DONA service determines 542 that the analysis is accurate and proceeds to the operation 508. Where the DONA service receives input indicating that the user would like to refine the analysis, the DONA service determines 542 that the analysis is not accurate and returns to the operation 538.

Returning to the operation 544, the DONA service determines 544 whether the user has requested help. For instance, in one example, the DONA service receives a notification from the virtual assistant that indicates the user entered input expressly requesting help from the DONA service. Where the DONA service determines 544 that help has not been requested, the process 500 ends. Where the DONA service determines 544 that help has been requested, the process 500 proceeds to operation 546.

In the operation 546, the DONA service displays 546, via the virtual assistant, elements selectable by the user to navigate DONA skills available to the user. These elements selectable by the user to indicate that that the user wishes to utilize a skill. These elements can include a hierarchical control for browsing a hierarchy that groups skills by subject area or one or more other commonalities and/or a search control that enables the user to search by sentiment and/or keyword. Next, the DONA service determines 548 whether the user selected a skill. Where the DONA service determines 548 that the user selected a skill, the DONA service proceeds to operation 510 as illustrated in FIG. 5B. Where the DONA service determines 548 that the user has not selected a skill, the DONA service returns to the operation 546.

Additional Examples

In at least one example, a DONA system (e.g., the DONA system 100 of FIG. 1) autonomously and proactively identifies that a user (e.g., the user 106 of FIG. 1) has a busy upcoming schedule and suggests some time skills that includes a calendar assistant skill. In this example, the user selects the calendar assistant skill for utilization.

More specifically, in this example, a DONA service (e.g., the DONA service 112 of FIG. 1) periodically transmits an analysis request to a recommendation engine (e.g., the recommendation engine 116 of FIG. 1). In response to reception of the analysis request, the recommendation engine interoperates with an email and calendar software application (e.g., MICROSOFT Outlook®) to retrieve records storing information regarding past and future calendar events for the user. The recommendation engine further determines (by comparing past calendar information with calendar information for the coming week) that the user's calendar is abnormally busy in the coming week. The recommendation engine returns an analysis response to the DONA service that indicates its findings.

In response to reception of the analysis response indicating the abnormally busy calendar of the user, the DONA service transmits a recommendation request to the recommendation engine. The recommendation request includes parameters specifying the user, and the keywords and sentiments such as "calendar" and –0.2. In response to reception of the recommendation request, the recommendation engine retrieves user profile records and skill profile records from a user profile data store (e.g., the user profile data store 126 of FIG. 1) and a skill profile data store (e.g., the skill profile data store 124 of FIG. 1). It should be noted that the skill profile data store includes entries for all DONA skills available to the user.

Further, in this example, the user profile records retrieved are associated with the user and the keywords and sentiments. The skill profile records retrieved are associated with keywords and sentiments and represent the experience of multiple users. The recommendation engine calculates a weight for each skill identified within the retrieved user and skill profile records. For any skill identified in both a user profile record and a skill profile record, the recommendation engine calculates a weight that is based on the weights included in both records. Next, the recommendation engine generates and transmits a recommendation response to the DONA service. In this example, the recommendation response includes a set of time skills including the calendar assistant and a smart to-do list.

In response to reception of the recommendation response, the DONA service transmits a prompt request to a virtual assistant (e.g., the virtual assistant 108 of FIG. 1). The prompt request instructs the virtual assistant to present the calendar assistant and the smart to-do list as selectable elements to the user. In this example, the user enters input selecting the calendar assistant, and the virtual assistant transmits a prompt response to the DONA service that indicates the user's selection of the calendar assistant by including an identifier of the calendar assistant.

In response to reception of the prompt response, the DONA service configures and initiates the calendar assistant. By default, the calendar assistant is configured to block out 20 to 100 percent of the user's remaining free calendar time, setup an out of office/delayed response message, notify the user's manager of the user's selection, automatically collate information for meetings that the user is scheduled to attend, and to run for 1 to 5 days. In this example, the DONA service interoperates with the virtual assistant (e.g., via prompt requests/responses) to confirm and/or modify the calendar assistant's default configuration. In response to completion of the configuration of the calendar assistant, the DONA service initiates and begins monitoring it. The calendar assistant interoperates with the email and communication software application via its API to implement its configuration.

Continuing this example, the DONA service monitors the user's utilization of and compliance with the calendar assistant by periodically accessing a DONA log data store (e.g., the DONA log data store 120 of FIG. 1). Upon the user's completion of the use of the calendar assistant, the DONA service prompts the user (via the virtual assistant) for feedback and stores any feedback received in a DONA feedback data store (e.g., the DONA feedback data store 122 of FIG. 1), and this example ends.

In at least one example, a DONA system (e.g., the DONA system 100 of FIG. 1) receives an utterance from a user (e.g., the user 106 of FIG. 1) that indicates the user is "stressed regarding their workload" and suggests recommends some focus skills that includes a Pomodoro skill. In this example, the user selects the Pomodoro skill for utilization.

More specifically, in this example, a virtual assistant (e.g., the virtual assistant 108 of FIG. 1) receives the utterance from the user and passes the utterance to a DONA service (e.g., the DONA service 112 of FIG. 1) for handling. In response to its reception, the DONA service passes the utterance to a DONA NLP service (e.g., the DONA NLP service 114 of FIG. 1) via a parse request. In response to its reception, the DONA NLP service processes the utterance and identifies the keyword "workload" and a sentiment of −0.4, generates a parse response including the keyword and the sentiment, and transmits the parse response to the DONA service.

In response to reception of the parse response indicating the mental state of the user via the keyword and sentiment, the DONA service transmits a recommendation request to the recommendation engine. The recommendation request includes parameters specifying the user, and the keyword and sentiment. In response to reception of the recommendation request, the recommendation engine retrieves user profile records and skill profile records from a user profile data store (e.g., the user profile data store 126 of FIG. 1) and a skill profile data store (e.g., the skill profile data store 124 of FIG. 1). It should be noted that the skill profile data store includes entries for all DONA skills available to the user.

Further, in this example, the user profile records retrieved are associated with the user and the keywords and sentiments. The skill profile records retrieved are associated with keywords and sentiments and represent the experience of multiple users. The recommendation engine calculates a weight for each skill identified within the retrieved user and skill profile records. For any skill identified in both a user profile record and a skill profile record, the recommendation engine calculates a weight that is based on the weights included in both records. Next, the recommendation engine generates and transmits a recommendation response to the DONA service. In this example, the recommendation response includes a set of focus skills including the Pomodoro skill and a mindfulness skill.

In response to reception of the recommendation response, the DONA service transmits a prompt request to a virtual assistant (e.g., the virtual assistant 108 of FIG. 1). The prompt request instructs the virtual assistant to present the Pomodoro skill and the mindfulness skill as selectable elements to the user. In this example, the user enters input selecting the Pomodoro skill, and the virtual assistant transmits a prompt response to the DONA service that indicates the user's selection of the Pomodoro skill by including an identifier of the Pomodoro skill.

In response to reception of the prompt response, the DONA service configures and initiates the Pomodoro skill. By default, the Pomodoro skill is configured to block selected notifications and control software application access of the user for specific time periods/intervals. In this example, the DONA service interoperates with the virtual assistant (e.g., via prompt requests/responses) to confirm and/or modify the Pomodoro skill's default configuration. In response to completion of the configuration of the Pomodoro skill, the DONA service initiates and begins monitoring it. The Pomodoro skill interoperates with an API exposed and implemented by a workspace client (e.g., the workspace client 102 of FIG. 1) to display a timer that tracks the current time interval, to disable notifications, and to control software application access according to the Pomodoro skill's configuration.

Continuing this example, the DONA service monitors the user's utilization of and compliance with the Pomodoro skill by periodically accessing a DONA log data store (e.g., the DONA log data store 120 of FIG. 1). Upon the user's completion of the use of the Pomodoro skill, the DONA service prompts the user (via the virtual assistant) for feedback and stores any feedback received in a DONA feedback data store (e.g., the DONA feedback data store 122 of FIG. 1), and this example ends.

Each of the processes disclosed herein each depict one particular sequence of acts in a particular example. Some acts are optional and, as such, can be omitted in accord with one or more examples. Additionally, the order of acts can be altered, or other acts can be added, without departing from the scope of the apparatus and methods discussed herein.

Computing Devices for DONA Mental Health and Performance Enhancement Systems

Figure 6:
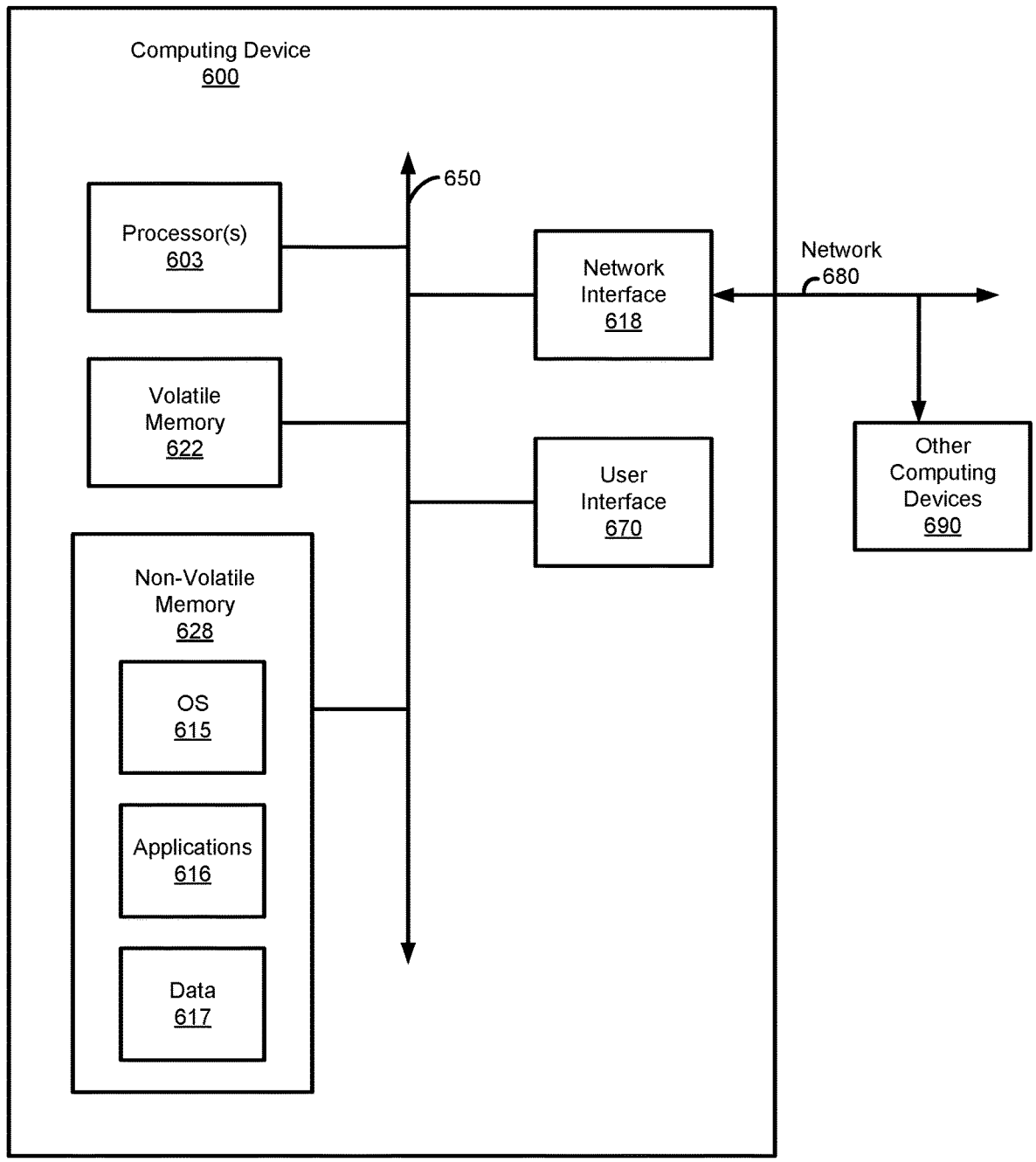
FIG. 6 is a block diagram of a network environment of computing devices in which one or more examples described herein can be implemented.

FIG. 6 is a block diagram of a computing device 600 configured to implement various mental health and performance enhancement systems and processes in accordance with examples disclosed herein.

The computing device 600 includes one or more processor(s) 603, volatile memory 622 (e.g., random access memory (RAM)), non-volatile memory 628, a user interface (UI) 670, one or more network or communication interfaces 618, and a communications bus 650. The computing device 600 may also be referred to as a client device, computing device, endpoint device, computer, or a computer system.

The non-volatile (non-transitory) memory 628 can include: one or more hard disk drives (HDDs) or other magnetic or optical storage media; one or more solid state drives (SSDs), such as a flash drive or other solid-state storage media; one or more hybrid magnetic and solid-state drives; and/or one or more virtual storage volumes, such as a cloud storage, or a combination of such physical storage volumes and virtual storage volumes or arrays thereof.

The user interface 670 can include a graphical user interface (GUI) (e.g., controls presented on a touchscreen, a display, etc.) and one or more input/output (I/O) devices (e.g., a mouse, a keyboard, a microphone, one or more speakers, one or more cameras, one or more biometric scanners, one or more environmental sensors, and one or more accelerometers, one or more visors, etc.).

The non-volatile memory 628 stores an OS 615, one or more applications or programs 616, and data 617. The OS 615 and the application 616 include sequences of instructions that are encoded for execution by processor(s) 603. Execution of these instructions results in manipulated data. Prior to their execution, the instructions can be copied to the volatile memory 622. In some examples, the volatile memory 622 can include one or more types of RAM and/or a cache memory that can offer a faster response time than a main memory. Data can be entered through the user interface 670 or received from the other I/O device(s), such as the network interface 618. The various elements of the device 600 described above can communicate with one another via the communications bus 650.

The illustrated computing device 600 is shown merely as an example client device or server and can be implemented within any computing or processing environment with any type of physical or virtual machine or set of physical and virtual machines that can have suitable hardware and/or software capable of operating as described herein.

The processor(s) 603 can be implemented by one or more programmable processors to execute one or more executable instructions, such as a computer program, to perform the functions of the system. As used herein, the term "processor" describes circuitry that performs a function, an operation, or a sequence of operations. The function, operation, or sequence of operations can be hard coded into the circuitry or soft coded by way of instructions held in a memory device and executed by the circuitry. A processor can perform the function, operation, or sequence of operations using digital values and/or using analog signals.

In some examples, the processor can be embodied in one or more application specific integrated circuits (ASICs), microprocessors, digital signal processors (DSPs), graphics processing units (GPUs), microcontrollers, field programmable gate arrays (FPGAs), programmable logic arrays (PLAs), multicore processors, or general-purpose computers with associated memory.

The processor(s) 603 can be analog, digital or mixed. In some examples, the processor(s) 603 can be one or more locally-located physical processors or one or more remotely-located physical processors. The processor(s) 603 can include multiple processor cores and/or multiple processors and can provide functionality for parallel, simultaneous execution of instructions or for parallel, simultaneous execution of one instruction on more than one piece of data.

The network interfaces 618 can include one or more interfaces to enable the computing device 600 to access a computer network 680 such as a Local Area Network (LAN), a Wide Area Network (WAN), a Personal Area Network (PAN), or the Internet through a variety of wired and/or wireless connections, including cellular connections and Bluetooth connections. In some examples, the network 680 may allow for communication with other computing devices 690, to enable distributed computing. The network 680 can include, for example, one or more private and/or public networks over which computing devices can exchange data.

In described examples, the computing device 600 can execute an application on behalf of a user of a client device. For example, the computing device 600 can execute one or more virtual machines managed by a hypervisor. Each virtual machine can provide an execution session within which applications execute on behalf of a user or a client device, such as a hosted desktop session. The computing device 600 can also execute a terminal services session to provide a hosted desktop environment. The computing device 600 can provide access to a remote computing environment including one or more applications, one or more desktop applications, and one or more desktop sessions in which one or more applications can execute.

Figure 7:
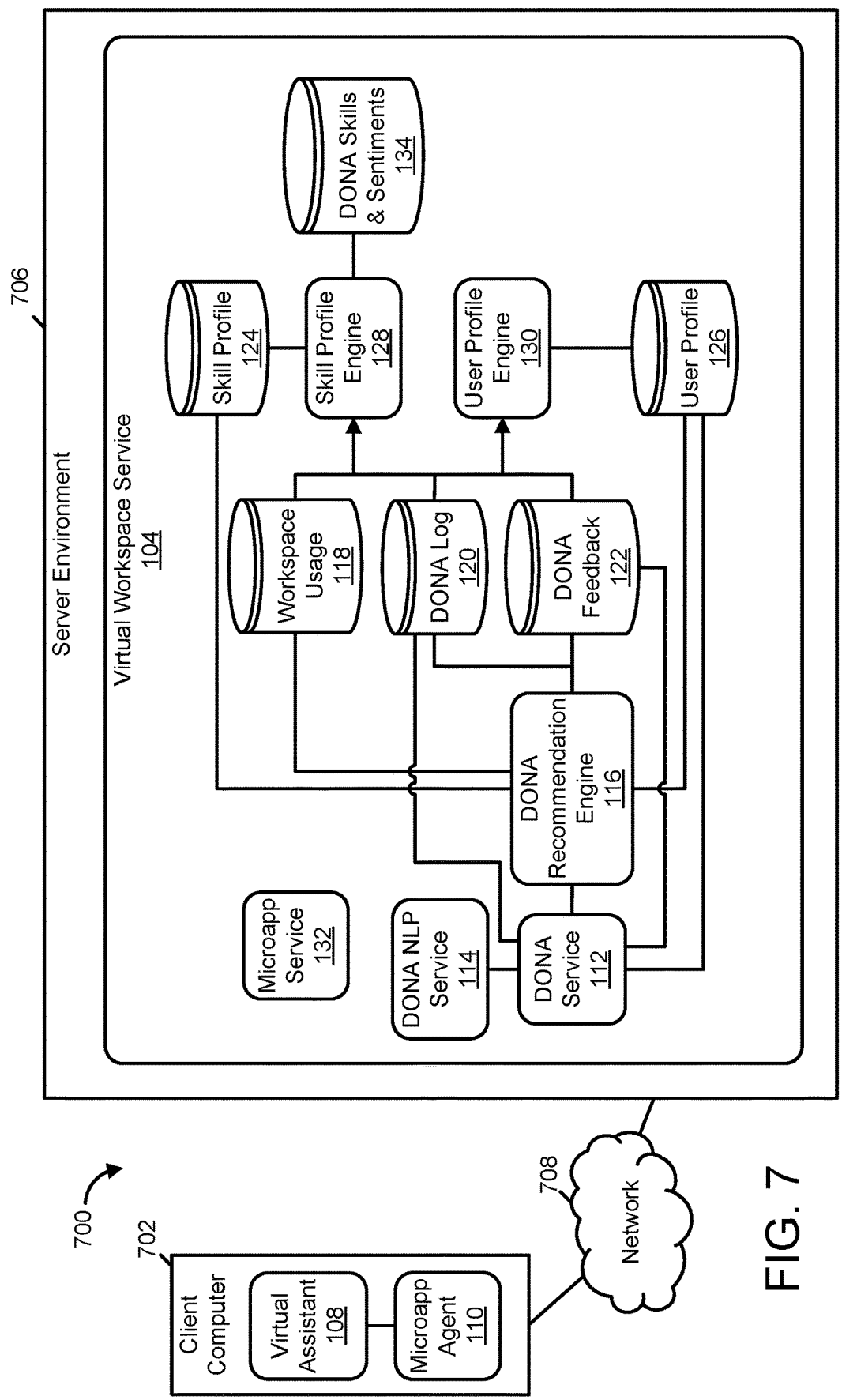
FIG. 7 is a block diagram of the mental health and performance system of FIG. 1 as implemented by a configuration of computing devices in accordance with one or more examples described herein.

FIG. 7 illustrates an mental health and performance enhancement system (e.g., the DONA system 100 of FIG. 1) configured for operation within a distributed computing system 700 comprising computing devices (e.g. the computing device 600 of FIG. 6). As shown in FIG. 7, the distributed computing system 700 includes a client computer 702 and a server environment 706. The client computer 702 and the server environment 706 are configured to interoperate with one another via a network 708. Each of the client computer 702, the server environment 706, and the network 708 include at least one computing device (e.g., the computing device 600 of FIG. 6). In some examples, the server environment 706 includes a plurality of computing devices structured as a cluster or other high availability, high bandwidth computing platform.

The client computer 702 is configured to host the virtual assistant 108 and the microapp agent 110 of FIG. 1. The server environment 706 is configured to host the DONA service 112, the DONA NLP service 114, the recommendation engine 116, the workspace usage data store 118, the DONA log data store 120, the DONA feedback data store 122, the skill profile data store 124, the user profile data store 126, the skill profile engine 128, the user profile engine 130, and the DONA skills and sentiments data store 134 of FIG. 1.

The distributed computing system 700 is but one example of many potential configurations that can be used to implement mental health and performance enhancement systems. As such, the examples disclosed herein are not limited to the particular configuration of computing device and other configurations are considered to fall within the scope of this disclosure.

Having thus described several aspects of at least one example, it is to be appreciated that various alterations, modifications, and improvements will readily occur to those skilled in the art. For instance, examples disclosed herein can also be used in other contexts. Such alterations, modifications, and improvements are intended to be part of this disclosure and are intended to be within the scope of the examples discussed herein. Accordingly, the foregoing description and drawings are by way of example only.

Also, the phraseology and terminology used herein is for the purpose of description and should not be regarded as limiting. Any references to examples, components, elements or acts of the systems and methods herein referred to in the singular can also embrace examples including a plurality, and any references in plural to any example, component, element or act herein can also embrace examples including only a singularity. References in the singular or plural form are not intended to limit the presently disclosed systems or methods, their components, acts, or elements. The use herein of "including", "comprising", "having", "containing", and variations thereof is meant to encompass the items listed thereafter and equivalents thereof as well as additional items. References to "or" can be construed as inclusive so that any terms described using "or" can indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

The invention claimed is:

1. A computer system comprising:
a memory storing a plurality of user profile records and a plurality of skill profile records;
a network interface; and
at least one processor coupled to the memory and the network interface and configured to:
provide a virtual workspace client;
monitor interactions between a user and one or more software applications accessed by the user via the virtual workspace client;
based on the interactions, generate a request to recommend a skill to improve performance of the user;
retrieve, from the plurality of user profile records, a user profile record associated with the user and the skill, the user profile record including a first weight indicative of one or more past experiences of the user with the skill;
retrieve, from the plurality of skill profile records, a skill profile record associated with the skill, the skill profile record including a second weight indicative of one or more past experiences with the skill of at least one user other than the user;
determine a third weight based on a combination of the first weight and the second weight;
generate a response to the request, the response including an identifier of the skill and the third weight; and
transmit the response to a virtual assistant configured to initiate the skill for the user.

2. The computer system of claim 1, the at least one processor being further configured to determine the first weight based on data generated by the interactions between the user and the one or more software applications.

3. The computer system of claim 2, the one or more software applications comprising one or more of a calendar application and a communications application.

4. The computer system of claim 1, the at least one processor being further configured to determine the second weight based on data generated by interactions between the at least one user other than the user and one or more software applications associated with the skill.

5. The computer system of claim 1, the at least one processor being further configured to:
prompt, via the virtual assistant, the user to enter input specifying feelings regarding work;
receive the input;
execute a natural language process on the input to identify one or more keywords and sentiments; and
generate the request to recommend the skill, the request including the one or more keywords and sentiments.

6. The computer system of claim 5, wherein
to retrieve the user profile record comprises to retrieve a user profile record associated with the user, the skill, and the one or more keywords and sentiments and
to retrieve the skill profile record comprises to retrieve a skill profile record associated with the skill and the one or more keywords and sentiments.

7. The computer system of claim 1, the at least one processor being further configured to:
configure the skill to the user; and
implement the skill using a microapp within the virtual workspace client.

8. The computer system of claim 7, the at least one processor being further configured to:
monitor utilization of the skill by the user;
prompt the user for feedback regarding the skill; and
store the feedback in the memory.

9. The computer system of claim 8, the at least one processor being further configured to determine the first weight based on the feedback.

10. The computer system of claim 9, the at least one processor being further configured to:
monitor utilization of the skill by the at least one user other than the user;
prompt the at least one user for other feedback regarding the skill; and
determine the second weight based on the other feedback.

11. A method of enhancing mental health and performance of a user of a virtual workspace client, the method comprising:
monitoring interactions between the user and one or more software applications accessed by the user via the virtual workspace client;
based on the interactions, generating a request to recommend a skill to improve the performance of the user;
retrieving, from a plurality of user profile records, a user profile record associated with the user and the skill, the user profile record including a first weight indicative of one or more past experiences of the user with the skill;
retrieving, from a plurality of skill profile records, a skill profile record associated with the skill, the skill profile record including a second weight indicative of one or more past experiences with the skill of at least one user other than the user;
determining a third weight based on a combination of the first weight and the second weight;
generating a response to the request, the response including an identifier of the skill and the third weight;
transmitting the response to a virtual assistant; and
via the virtual assistant, configuring the skill for implementation using a microapp within the virtual workspace client.

12. The method of claim 11, further comprising:
prompting, via the virtual assistant, the user to enter input specifying feelings regarding work;
receiving the input;
executing a natural language process on the input to identify one or more keywords and sentiments; and
generating the request to recommend the skill, the request including the one or more keywords and sentiments.

13. The method of claim 12, wherein
retrieving the user profile record comprises retrieving a user profile record associated with the user, the skill, and the one or more keywords and sentiments, and
retrieving the skill profile record comprises retrieving a skill profile record associated with the skill and the one or more keywords and sentiments.

14. The method of claim 13, further comprising:
monitoring utilization of the skill by the user;
prompting the user for feedback regarding the skill; and
storing the feedback in memory.

15. The method of claim 14, further comprising determining the first weight based on the feedback.

16. The method of claim 15, further comprising:
monitoring utilization of the skill by the at least one user other than the user;
prompting the at least one user for other feedback regarding the skill; and
determining the second weight based on the other feedback.

17. A non-transitory computer readable medium storing executable sequences of instructions to implement a mental health and performance enhancement process within a virtual workspace, the sequences of instructions comprising instructions to:
monitor interactions between a user and one or more software applications accessed by the user via the virtual workspace client;
based on the interactions, generate a request to recommend a skill to improve performance of the user;
retrieve, from the plurality of user profile records, a user profile record associated with the user and the skill, the user profile record including a first weight indicative of one or more past experiences of the user with the skill;
retrieve, from the plurality of skill profile records, a skill profile record associated with the skill, the skill profile record including a second weight indicative of one or more past experiences with the skill of at least one user other than the user;
determine a third weight based on a combination of the first weight and the second weight;
generate a response to the request, the response including an identifier of the skill and the third weight; and
transmit the response to a virtual assistant configured to initiate the skill for the user.

18. The non-transitory computer readable medium of claim 17, the sequences of instructions further comprising instructions to:
prompt, via the virtual assistant, the user to enter input specifying feelings regarding work;
receive the input;
execute a natural language process on the input to identify one or more keywords and sentiments; and generate the request to recommend the skill, the request including the one or more keywords and sentiments.

19. The non-transitory computer readable medium of claim 18, the sequences of instructions further comprising instructions to:
monitor utilization of the skill by the user;
prompt the user for feedback regarding the skill; and
determine the first weight based on the feedback.

20. The non-transitory computer readable medium of claim 19, the sequences of instructions further comprising instructions to:
monitor utilization of the skill by the at least one user other than the user;
prompt the at least one user for other feedback regarding the skill; and
determine the second weight based on the other feedback.

* * * * *